United States Patent [19]

Noto

[11] Patent Number: 4,656,049
[45] Date of Patent: Apr. 7, 1987

[54] METHOD AND APPARATUS FOR THE PROPER QUANTIZED APPLICATION OF A MOLD RELEASE AGENT ONTO A MOLD SURFACE

[75] Inventor: Vincent H. Noto, San Diego, Calif.

[73] Assignee: General Dynamics Corp. Space Systems Division, San Diego, Calif.

[21] Appl. No.: 837,995

[22] Filed: Mar. 10, 1986

[51] Int. Cl.$^4$ .................. B05C 11/00; B05D 3/06; B44D 1/20; G01N 21/64

[52] U.S. Cl. .................. 427/10; 118/323; 118/665; 118/713; 250/461.1; 427/54.1; 427/133; 427/135

[58] Field of Search .................. 427/8–10, 427/54.1, 133–135; 118/712, 713, 323, 665; 250/459.1, 461.1

[56] References Cited

U.S. PATENT DOCUMENTS 4,473,403  9/1984  Wesala ..................... 427/135 X
4,491,607  1/1985  Wesala ..................... 427/135

Primary Examiner—Michael R. Lusignan
Attorney, Agent, or Firm—John R. Duncan; Frank D. Gilliam

[57] ABSTRACT

Disclosed is a method of placing a measured amount of tracer material into a release agent solution so that the concentration of tracer material in the release agent as applied to a mold surface is an indication of the amount and distribution of the release agent on the mold surface. The release agent can be applied and/or re-applied until the amount of the tracer material reaches a predetermined value. In the embodiment disclosed the tracer material is a UV dye which will re-emit light when activated by a UV light source and the intensity level of the re-emitted light is a function of the amount of release agent applied.

Curing of the release agent preferably taken place after each layer in multiple layer applications.

Also disclosed is a spray head (12) connected to a source (20) of release agent with UV dye therein for coating a mold surface (28). A source of UV light (30,32) activates the UV dye to re-emit visable light which is measured by a photometer (34) to practice the above method.

Also disclosed is a method and apparatus by which release agent degradation can be detected and corrected before the release agent is applied to the mold surface.

Also disclosed is a completely automatic release agent application cell wherein a release agent spraying robot (10) and a traveling oven (62) automatically processes mold surfaces with a release agent under the operation and control of a computer (64).

18 Claims, 4 Drawing Figures

METHOD AND APPARATUS FOR THE PROPER QUANTIZED APPLICATION OF A MOLD RELEASE AGENT ONTO A MOLD SURFACE

BACKGROUND OF THE INVENTION

This invention relates, in general, to molds and molding processes and is specifically directed to a method and apparatus for applying release agents to surfaces of molds.

The purpose of release agents applied to mold surfaces is, of course, well known but the proper application of the release agent to the mold surface has been difficult to achieve. Often the release agent was not applied uniformly across the surface of the mold with the result that the molded article, such as a composite article, sometimes stuck totally or in part to the mold surface. This non-uniformity of distribution of the coating was due to a number of things—partial or complete clogging, intermittent clogging, of the applicator (spray-gun) used to apply the release agent, a degraded release agent, or simply the inability to determine the non-uniformity of the coating, visually or otherwise. Thus, there is a need to measure the amount of release agent applied to a mold surface in a quantitative manner and it is one of the objects of this invention to provide such a method.

It will be apparent to those skilled in the art that, in practicing such a method, robotics is possible and it is another object of this invention to provide an apparatus by which the proper amount of release agent is automatically applied to a mold surface.

In addition to the inability to properly apply the release agent to the mold surface, prior methods suffered under the drawback of the degradation of the release agent before and during application, as mentioned above. This degradation decreased and release characteristics of the release agent, or inactivated the release agent, thus inhibiting the proper release characteristics of the coating after cure.

It is therefore another object of this invention to provide a method and apparatus which provides for release agent degradation detection and correction and which detects and corrects this degradation in-line (in real time) so that this latter method may also be a part of the automation of the first method.

In the practice of the foregoing method and apparatus a completely automatic mold release cell is needed which will take molds, coat them with a release agent, bake (cure) them, or recoat them and rebake them the appropriate number of times, before releasing the properly treated molds. This would completely release human involvement in the application of the desired amount of release agent onto the mold and in the transport of the mold to and from oven areas where the release agents are cured. Thus it is still another object of this invention to provide such an apparatus.

SUMMARY OF THE INVENTION

The method and apparatus which attains the foregoing objects comprises a method of placing a measured amount of tracer material (fluorescing dye, in this case a UV dye) into the release agent solution so that the amount of re-emission of energy (light) by the tracer material when activated by an energy source (UV light source) is proportional to the tracer material present as an indication of the amount and distribution of the release agent on the mold surface. The coating of release agent will be applied and/or re-applied until the intensity level of the emitted energy (light) reaches a predetermined value as measured by a sensing device (photometer).

The finalized layer of release agent is preferrably used, and if multiple layers are applied, curing after each layer is preferred.

The invention also includes a method and apparatus by which release agent degradation can be detected. This includes the step of taking a turbidity measurement of the release agent solution before it is applied to the mold surface. If the release agent solution is found to be turbid, the solution is not used and a fresh non-degraded solution will be used. An apparatus is provided for making the turbidity measurements and for bypassing the degraded release solution so that non-degraded material only may be used for application (spray) onto the mold.

Also as part of this invention, there is provided a completely automatic release agent application cell in which the mold is placed in a spraying area fitted with a release agent spraying robot and a traveling oven (infrared or circulating hot air). A bar code on the mold informs a computer of the specific treatment and number of repeat cycles necessary to produce an acceptable release agent surface on the mold before the mold is released for use. This latter method and apparatus totally replaces human involvement in the application of the release agent to the mold and in the transportation of the mold to and from oven areas.

DETAILED DESCRIPTION

Figures 1, 2:
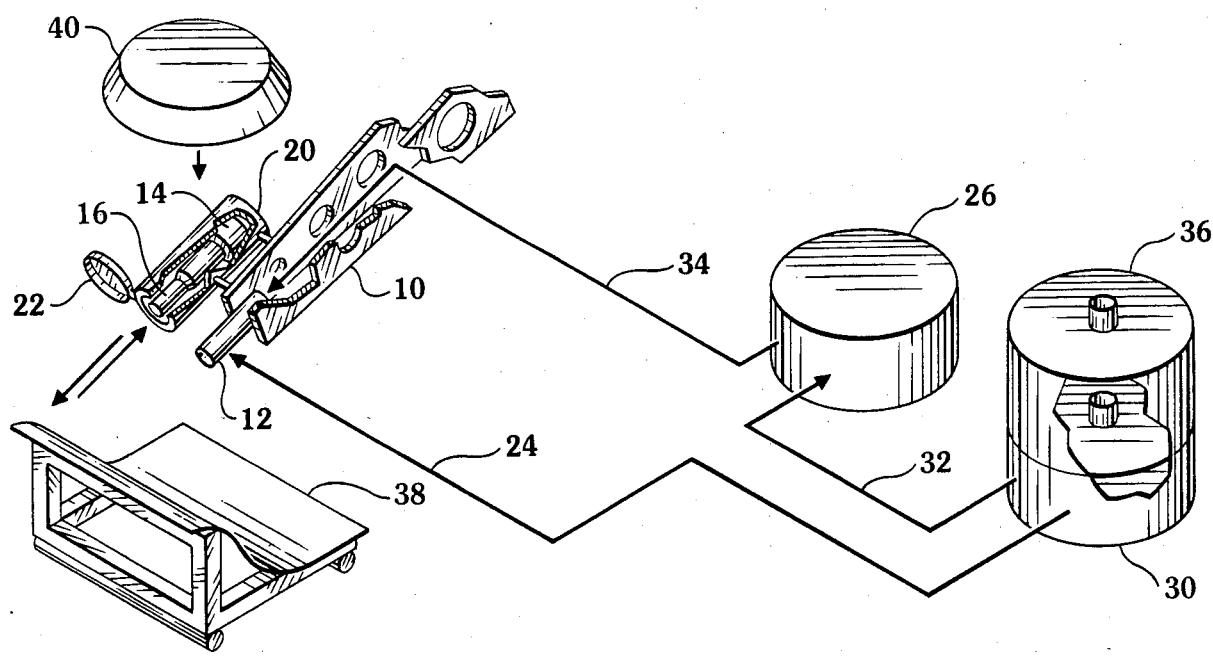
FIG. 1 is a flow diagram depicting the method of this invention for quantizing the application of a mold release agent to a mold.
FIG. 2 is a schematic illustration of an automatic means for applying a coating of the release agent to a mold and a means for measuring the concentration and distribution of the applied coating.

In FIGS. 1 and 2, there is disclosed a method and apparatus for measuring the amount of release agent applied to a mold surface in a quantitative manner. According to this invention, the amount of release agent applied (spray) in any coat and the total amount of mold release applied can be measured by determining the tracer material concentration on the mold surface by using a sensing device. In the preferred embodiment the tracer material is a fluorescing dye (UV dye) which is diluted to an appropriate preselected concentration and placed in the release agent solution, a polysiloxane mold release, preferably Frekote-44. The UV dye absorbs UV energy (light) when directed on a mold surface and re-emits this light in the visible region which is then measured by the sensing device. The amount of re-emission is proportional to the amount of UV dye present, and distinct differences in the emitted light intensity can be measured from one application of release agent to the next. The areas of the surface that are not as heavily coated as others will stand out as dark areas and can be recoated until the intensity level is similar across the entire mold surface. The coating is thus applied until the intensity level of the light emitted from the surface reaches a predetermined value as measured by the sensing device. The quantizing ability of this method will permit a robotic (automatic) type spray operation to be possible. The robotized spray can then both spray and check its application for spray pattern abnormalities (light and dark areas) on the mold surface.

After the mold is coated satisfactorily, it is preferrably cured, if multiple coatings are applied, curing after each satisfactory coating is preferred.

FIG. 2 illustrates apparatus for practicing the method thus described. In this figure, there is shown a robot arm 10 with a spray head 12, light source 14 and photometer 16 located on the robot arm. The light source 14 and photometer 16 are in a reflector housing 20. The latter has a swing-away shutter 22 to protect the light source and photometer from possible spray contamination. The spray head is are attached to a line 24 (flexible tube) under high pressure from a pump 26 for pumping and conveying release agent solution from a drum 30. A feedline 32 is located between the drum 30 and the pump 26 and a return line 34 for excess or degraded release agent is connected between the spray head 12 and the drum 30. The drum 30 is sealed but connected to a drying container 36 containing dessicate. The spray head 12 may be automatically operated, as stated above, or manually operated, and, is moveably positioned to spray a mold surface 38 of a mold, a composite mold for example. The tracer material (fluorescing dye) in the release agent is activated by UV light from either or both of two light sources; the mold, the first light source 14 is directed to the mold surface 38 and a second light source located above and directed onto the mold surface 38. The re-emitted light from the mold surface 38 is measured by the photometer 16 which also may be automated or manually operated for measuring and controlling the amount of release agent applied to the mold surface 38. Again, the distinct differences in the light intensity are measured by the photometer 16. Any areas that are not as heavily coated as others will stand out as dark areas, identified, and subjected to being re-coated. If the spray head 12 is automatically controlled, this method can be robotized (automatically quantized).

Figure 3:
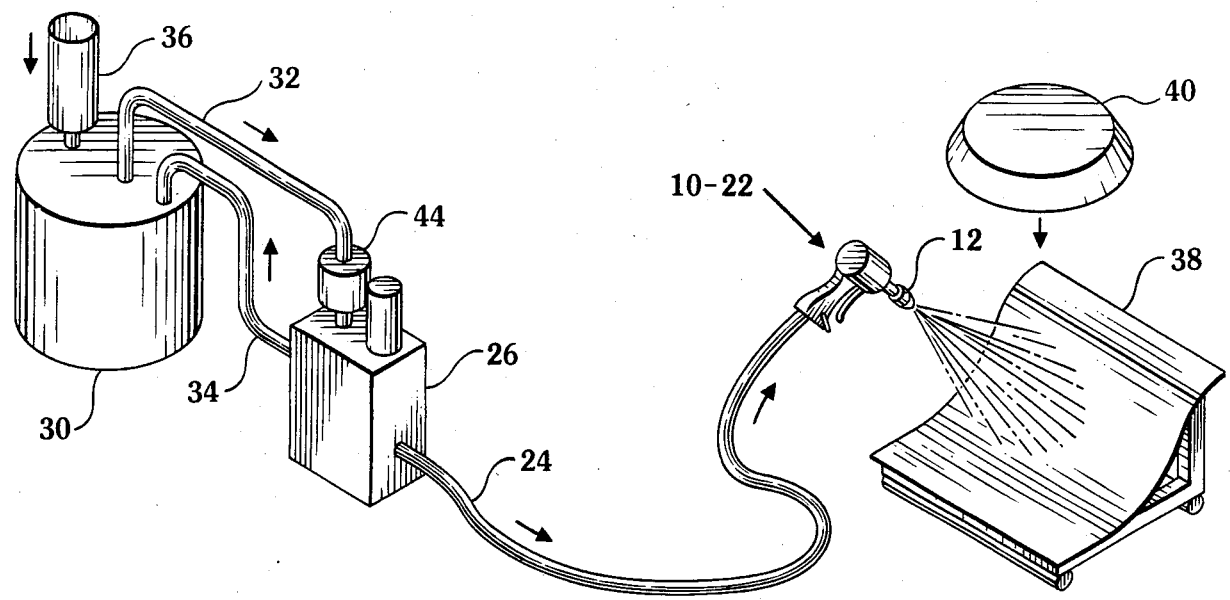
FIG. 3 illustrates a means for measuring and correcting the degradation of the release agent before it is directed to the applicator for application onto the mold surface.

With the foregoing spray head 10 and its attendant apparatus, fresh non-degraded release agent must be used. Unfortunately polysiloxane mold release solutions, such as Frekote-44, have the drawback of being water sensitive. the siloxane polymerizes in a degraded fashion and precipitates out of solution. The amount of precipitation is an indication of the degradation that has occurred. In this invention before the release agent is sprayed onto the mold surface, a turbidity test is carried out on the solution and if the solution is turbid, a warning signal is generated and the automatic equipment for spraying the release will be stopped. FIG. 3 illustrates an apparatus for carrying out this process. In FIG. 3, those components having the same function as in FIG. 2 are given the same reference numeral to simplify the description of this figure. In this figure, the spray head 12 is positioned with respect to the mold surface 38 as in FIG. 2 and the high pressure line 24 is connected to the pump 26 as before. However, before the mold release solution is fed into the inlet of the pump 26, a turbidity meter (nephelometer) 42, placed in the feed line 32 between the drum 30 and the pump 26 measures the turbidity of the solution. If the solution is found to be turbid, a warning signal is produced to warn the operator of the spray gun not to spray and the degraded release agent is returned to the drum 30 via return line 34. If the system is automated, the signal produced by the turbidity meter 44 will actuate a bypass valve (not shown) to direct the degraded release agent back to the drum 30 via the return line 34. Measurement of the release agent can be made at the time of spraying or at selected timed intervals according to the experience of the operator with the release agent being used. The advantage of this system is the preservation of the mold surface 38 by only coating it with fresh release agent thus requiring less rework.

Figure 4:
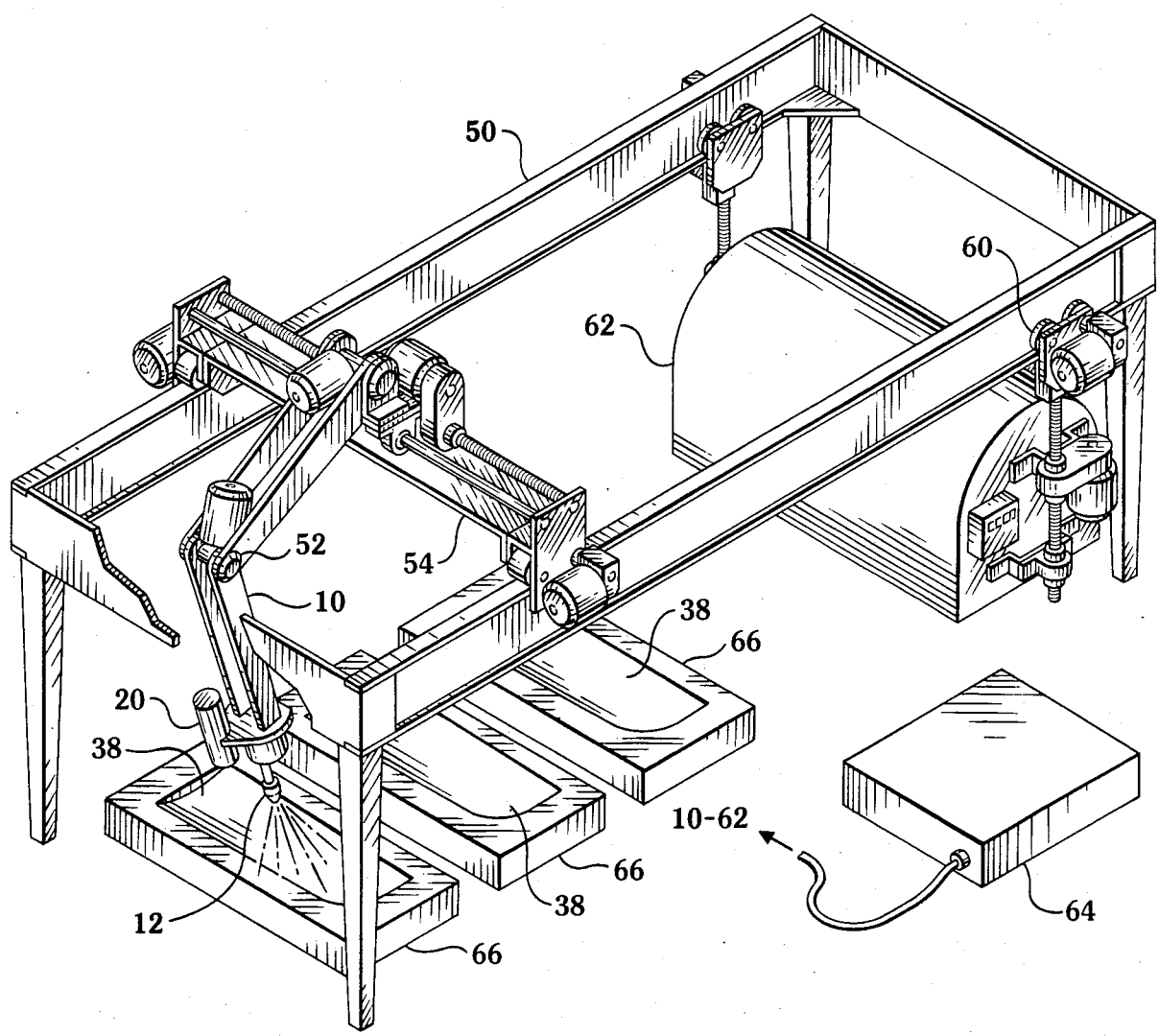
FIG. 4 is a schematic illustration of a completely automatic mold release agent application cell utilizing the method and apparatus of FIGS. 1-3.

Utilizing the automatic version of the spray gun, also referred to as the robotized version or simply a robot, with its automatic measuring system for controlling the amount and distribution of the release agent on the mold surface 38 as described in connection with FIG. 2 and with its automatic turbidity measuring device as described in connection with FIG. 3, these two devices can be used in a completely automatic mold release agent cell which will take molds, coat them with a mold release agent, bake the molds, coat and rebake them for the appropriate number of times and then release the treated molds. Such a cell is shown in FIG. 4 and identified by the reference numeral 50. The spray head 12 light source 14 and photometer 16 within reflector housing 20 are shown mounted on the traveling robot arm 10 as part of an overhead type traveling gantry crane 54 for movement in various directions to position the spray head 12 of reflector housing 20 where desired. A second overhead type traveling gantry crane 60 is connected to an oven 62 which also moves the oven 62 in various directions to position the oven where desired. Not shown to simplify this figure are the drum 30; the turbidity meter 44; etc. for the spray head 12. Also not shown is the infrared or hot air head source for the oven 62. All elements of the cell 50 are connected to an controlled by a computer and computer terminal 64 as indicated by the connector arrow 10-62.

Molds are placed into a spraying area 66. Each mold, being provided with a bar code which is read by the robot 10 and the bar code informs the computer of the specific treatment and the number of repeat cycles necessary to make an acceptable release coated surface on the mold. The robotized spray head 12 sprays the release agent on the mold and identifies the tracer material concentration as described above. If the application of release agent is even and sufficient, the robot moves away from the spray mold and the traveling heating element 62 passes over the treated mold. The mold surface is heated until the release agent reaches the proper degree of heat treatment and then the oven backs away. Again, all components are under the control of the computer. If necessary, the robot returns for additional spraying and when the mold is determined to be properly coated and heat treated, the treated mold is then removed from the cell 50.

I claim:
1. A method of measuring the amount of release agent applied to the surface of a mold comprising the steps of,
   placing a known amount of tracer material in the release agent,
   applying said release agent including said tracer material onto said surface, measuring the concentration of tracer material on said surface as an indication of the amount and distribution of the release agent on said surface.

2. The method as claimed in claim 1 including the further step of continuing to apply said release agent to said surface until the concentration of tracer material on said surface reaches a predetermined value.

3. The method as shown in claim 2 further including the step of curing said release agent.

4. The method as claimed in claim 1 further including the step of continuing to apply said release agent in certain areas and not in others until the concentration of tracer material is the same throughout the area of said surface.

5. The method as claimed in claim 1 wherein said tracer material is a material which reacts to energy applied thereto and then including the further step of directing energy onto said surface and measuring the intensity level of the reaction as an indication of the amount and distribution of the release agent on said surface.

6. The method as claimed in claim 5 including the step of continuing to apply said release agent in certain areas and not in others until the predetermined value of said reaction is the same throughout the total area of said surface.

7. The method as claimed 1 wherein said tracer material is a fluorescing dye and then including the step of directing a light of a known characteristic onto said surface and measuring the intensity level of the re-emitted light from said surface as an indication of the amount and distribution of the release agent on said surface.

8. The method as claimed in claim 7 including the further step of continuing to apply said release agent in certain areas until the intensity of the re-emitted light from said surface reaches a predetermined value is the same throughout the total area of said surface.

9. The method as claimed in claim 8 wherein said fluorescing dye is ultraviolet and where the light source is an ultraviolet light source.

10. A method of measuring the amount of release agent applied to the surface of a mold comprising the steps of,
    placing a known amount of UV dye in the release agent solution,
    spraying said release agent including said UV dye onto said surface,
    directing a UV light source onto said surface,
    measuring the concentration of UV dye as a function of the amount of release agent applied to the surface by measuring the visible light emitted from said surface, and
    continuing to spray said surface with release agent until the entire surface is coated with the selected amount of release agent according to the intensity of the visible light emitted from said surface.

11. The method as claimed in claim 10 including the further step of curing the applied release agent.

12. An apparatus for coating a measured amount of release agent having a predetermining amount of tracer material therein onto a mold surface comprising,
    a spray gun connected to a source of release agent solution and positioned to spray a coat of release agent onto the mold surface,
    means for activating a tracer material in said release agent on said mold surface, and
    means for measuring the activation of said tracer material to determine the amount and distribution of the coating sprayed on said mold surface.

13. The apparatus claimed in claim 12 further including means for controlling the output of said spray gun according to the reaction of said tracer material.

14. The apparatus as claimed in claim 12 wherein said tracer material is a UV dye, the means for activating the tracer material is a UV light source and the means for measuring the quantity and distribution of said coating is a photometer.

15. The apparatus as claimed in claim 13 further including means for determining the quality of the release agent being fed to the spray gun and means for bypassing any unqualified release agent back to the release agent source.

16. The apparatus claimed in claim 14 wherein said means for determining the quality of the release agent is a nephelometer.

17. An apparatus for coating a mold surface with a predetermined amount of release agent, said release agent having a UV dye of a known amount therein, said apparatus including,
    applicator means for coating said mold surfaces,
    means for directing UV light toward said mold surface,
    means for measuring the re-emitted light from said mold surface as a function of the quantity and distribution of said coating mold,
    heating means for heat treating said coating material,
    means for moving said applicator means to and from a position to apply said release agent to said mold surface, and
    means for moving said heating means to and from said mold surface to be treated.

18. The apparatus as claimed in claim 17 further including computer means to control the movement and operation of said applicator means and said heating means.

* * * * *